United States Patent
Schulten et al.

(10) Patent No.: US 8,367,421 B2
(45) Date of Patent: Feb. 5, 2013

(54) GAS DETECTOR TUBE FOR DETERMINING BENZENE

(75) Inventors: Armin Schulten, Hemmelsdorf (DE); Silke Guga, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 192 days.

(21) Appl. No.: 13/029,599

(22) Filed: Feb. 17, 2011

(65) Prior Publication Data

US 2011/0236987 A1  Sep. 29, 2011

(30) Foreign Application Priority Data

Mar. 24, 2010 (DE) .......... 10 2010 012 468

(51) Int. Cl.
*G01N 33/00* (2006.01)
(52) U.S. Cl. ......... 436/140; 436/164; 436/168; 436/169
(58) Field of Classification Search .......... None
See application file for complete search history.

(56) References Cited

FOREIGN PATENT DOCUMENTS

| DE | 865 384 B | 2/1953 |
|---|---|---|
| DE | 10 09 827 B | 6/1957 |
| DE | 10 12 480 B | 7/1957 |
| DE | 16 98 176 B1 | 5/1972 |

OTHER PUBLICATIONS

Cheng et al., INSPEC, abstract nr. 8994506, 2006, "Investigation of element and modifying properties of sensitive material response to benzene hydrocarbon", Chinese Journal of Sensors and Actuators, 2006, vol. 19, blz. 559-601.

Pei et al., INSPEC, abstract nr. 8202494, 2004, "Investigation of properties of [gamma]-Fe2O3 sensitive material response to benzene hydrocarbon", Journal of Functional Materials and Devices, 2004, vol. 10, blz. 41-44.

*Primary Examiner* — Robert Xu
(74) *Attorney, Agent, or Firm* — McGlew and Tuttle, P.C.

(57) ABSTRACT

An improved detection reaction for benzene in gas analysis with a gas detector tube formed of a carrier material impregnated with gold(III) oxide in a display layer.

20 Claims, 1 Drawing Sheet

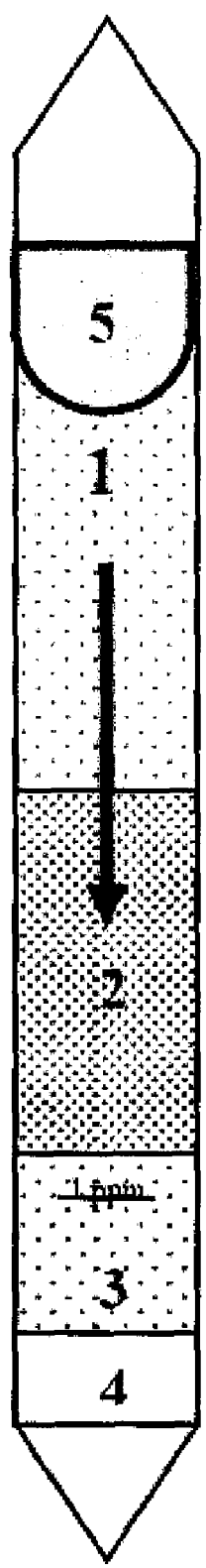

GAS DETECTOR TUBE FOR DETERMINING BENZENE

CROSS REFERENCE TO RELATED APPLICATIONS

This application claims the benefit of priority under 35 U.S.C. §119 of German Patent Application DE 10 2010 012 468.0 filed Mar. 24, 2010, the entire contents of which are incorporated herein by reference.

FIELD OF THE INVENTION

The present invention pertains to a gas detector tube and to a process for determining benzene.

BACKGROUND OF THE INVENTION

The gas analysis of benzene gas mixtures by means of gas detector tubes has hitherto been carried out colorimetrically on the basis of p-quinoid compounds with paraformaldehyde/sulfuric acid or with iodine pentoxide. The determination with $I_2O_5$ yields full, sharp display, which can be read by the user with certainty. The sensitivity of 2 ppm of benzene and the selectivity against, e.g., gasoline hydrocarbons are, however, insufficient.

A process for detecting benzene in gases, which comprises the reacting of the gas to be tested with a mixture of paraformaldehyde and anhydrous sulfuric acid, which said mixture is preferably applied to silica gel, is known from DE 865 384 B. The sensitivity of the detection reaction can be increased by adding dimethyl sulfate. The detection on the basis of paraformaldehyde/sulfuric acid is selective and sensitive enough in its application with a detection limit of about 0.5 ppm of benzene. However, the display accuracy is insufficient because of a diffuse change in color, so that the user can read the concentration displayed in an only poorly defined manner. In addition, the measurement times with 20 minutes and 20 strokes are not user-friendly and not accepted in the container fumigation market. Said tubes cannot be used for release measurements, e.g., in the container fumigation market because of poor sensitivity, reading accuracy, measurement time and selectivity. A qualitative measurement, which provides information on whether a container can be safely accessed or not, is required for this application.

SUMMARY OF THE INVENTION

The basic object of the present invention is to provide an improved detection reaction for benzene in gas analysis with a gas detector tube as well as a corresponding process.

According to the invention, a gas detector tube is provided for detecting benzene. The detector tube comprises a display layer which consists essentially of a carrier material impregnated with gold(III) oxide.

According to a further aspect of the invention, a process is provided for detecting benzene in a gas sample. The process comprises the steps of providing a gas detector tube with a display layer which consists essentially of a carrier material impregnated with gold(III) oxide and passing the gas sample into the gas detector tube such that the gas sample is reacted with the carrier material impregnated with gold(III) oxide.

According to still another aspect of the invention the process further comprises using the gas detector tube to detect benzene in the gas sample by observing a change in color in the display layer.

Gas analyses with gas detector tubes, which have a display layer based on gold(III) oxide, yield a sharp, easy-to-read, selective blackish-purple display. Gasoline hydrocarbons, e.g., 800 ppm of n-octane, do not interfere with the display of benzene, and aromatics, e.g., toluene or xylene, are retained in a benzene-permeable absorption layer acting as a prelayer and displayed to the user qualitatively with a brownish-purple change in color.

The gas detector tube also has, in addition to the benzene-permeable absorption layer, a dry layer, which is arranged upstream of the absorption layer.

The dry layer consists in the known manner of silica gel impregnated with 100% sulfuric acid. It binds the humidity of the air and protects the moisture-sensitive absorption and display layer.

The absorption layer consists of silica gel, which is impregnated with 100% sulfuric acid and selenium dioxide. It oxidizes toluene and xylene, so that these cannot enter the display layer and react with gold(III) oxide there. The presence of toluene and xylene is qualitatively displayed in this layer with a brownish-purple change in color. The absorption layer is already used in prior-art gas detector tubes with another detection reaction.

The display layer consists of quartz glass grit impregnated with 100% sulfuric acid and gold(III) oxide. The gold(III) oxide dissolved in sulfuric acid reacts with benzene into colloidal gold and is selectively displayed with a blackish-purple change in color. Based on the high price of gold oxide and the especially complicated preparation of the carrier by means of cleaning with aqua regia, the display layer is filled only to the extent, approximately 13 mm, that only a concentration of, e.g., 1 ppm can be displayed with 6 strokes with a stroke volume of 100 mL after 4 minutes. Concentrations of, e.g., 0.5 ppm and 2 ppm are correspondingly displayed with 12 strokes and 3 strokes.

Since the quantity of display layer needed is limited by the short filling, the tube can be manufactured cost-effectively despite high manufacturing costs. Alternative materials for the carrier materials are gelatinous silica and silica gel.

The display layer advantageously has a length between 10 mm and 15 mm at an internal diameter of the glass flask of between 1 mm and 3 mm. The length of the display layer is selected to be such that a change in color takes place in the display layer at a sample gas volume of approximately 1.2 L at a benzene concentration of 0.5 ppm.

The process according to the present invention for detecting benzene in a gas sample is characterized in that the gas sample is reacted with a carrier material impregnated with gold(III) oxide. Gold(III) oxide dissolved in sulfuric acid is used for the impregnation.

An advantageous use of a carrier material impregnated with gold(III) oxide in the display layer of a gas detector tube is the detection of benzene.

An exemplary embodiment of the gas detector tube according to the present invention is shown in the figure and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWING

In the drawing:

FIG. 1 is a schematic view showing a gas detector tube for detecting benzene.

DESCRIPTION OF THE PREFERRED EMBODIMENTS

Referring to the drawing in particular, the only figure schematically shows a gas detector tube for detecting benzene.

The gas detector tube includes a tube structure that allows flow therethrough, in a flow direction indicated by the arrow in FIG. 1. The gas detector tube has, in the direction of gas flow indicated by the arrow, a dry layer 1, an absorption layer 2 and a display layer 3 impregnated with gold(III) oxide. The sorption layers—the dry layer 1, the absorption layer 2 and the display layer 3—are held by a ceramic holding element 4 and by a wire hat 5.

The display layer 3 consists of a carrier material impregnated with the gold(III) oxide. The carrier material consists essentially of one or more of quartz glass, gelatinous silica or silica gel. The impregnation is gold(III) oxide dissolved in sulfuric acid.

The absorption layer 2 is for oxidizing toluene and xylene. The absorption layer 2 is arranged directly upstream of the display layer 3 in the embodiment of FIG. 1. The absorption layer 2 may advantageously consist essentially of carrier material impregnated with sulfuric acid and selenium oxide.

The dry layer 1 is arranged upstream of the absorption layer 2. The dry layer may advantageously consist essentially of a carrier material impregnated with sulfuric acid.

The display layer 3 may advantageously have a length between 10 mm and 15 mm at an internal diameter of between 1 mm and 3 mm. The length of the display layer 3 is selected to be such that a change in color takes place in the display layer 3 at a benzene concentration of 0.5 ppm at a sample gas volume of 1.2 L.

According to the process of the invention, the gas sample is reacted with a carrier material impregnated with gold(III) oxide. The gold(III) oxide dissolved in the sulfuric acid is used as the impregnation.

While specific embodiments of the invention have been described in detail to illustrate the application of the principles of the invention, it will be understood that the invention may be embodied otherwise without departing from such principles.

What is claimed is:

1. A gas detector tube for detecting benzene, the detector tube comprising:
   a display layer which consists essentially of a carrier material impregnated with gold(III) oxide.

2. A gas detector tube in accordance with claim 1, wherein the carrier material consists essentially of one or more of quartz glass, gelatinous silica and silica gel and the impregnation is gold(III) oxide dissolved in sulfuric acid.

3. A gas detector tube in accordance with claim 1, further comprising an absorption layer for oxidizing toluene and xylene, the absorption layer being arranged upstream of the display layer.

4. A gas detector tube in accordance with claim 3, wherein the absorption layer consists essentially of a carrier material impregnated with sulfuric acid and selenium oxide.

5. A gas detector tube in accordance with claim 3, further comprising a dry layer arranged upstream of the absorption layer.

6. A gas detector tube in accordance with claim 5, wherein the dry layer consists essentially of a carrier material impregnated with sulfuric acid.

7. A gas detector tube in accordance with claim 1, wherein the display layer has a length between 10 mm and 15 mm and an internal diameter of between 1 mm and 3 mm.

8. A gas detector tube in accordance with claim 1, wherein a length of the display layer is selected to be such that a change in color takes place in the display layer at a benzene concentration of 0.5 ppm at a sample gas volume of 1.2 L.

9. A process for detecting benzene in a gas sample, the process comprising the steps of:
   providing a gas detector tube with a display layer which consists essentially of a carrier material impregnated with gold(III) oxide; and
   passing the gas sample into the gas detector tube such that the gas sample is reacted with the carrier material impregnated with gold(III) oxide.

10. A process in accordance with claim 9, wherein gold(III) oxide dissolved in sulfuric acid is used as the impregnation.

11. A process in accordance with claim 9, wherein the carrier material consists essentially of one or more of quartz glass, gelatinous silica and silica gel and the impregnation is gold(III) oxide dissolved in sulfuric acid.

12. A process in accordance with claim 11, further comprising providing the gas detector tube with an absorption layer for oxidizing toluene and xylene, the absorption layer being arranged upstream of the display layer.

13. A process in accordance with claim 12, wherein the absorption layer consists essentially of a carrier material impregnated with sulfuric acid and selenium oxide.

14. A process in accordance with claim 12, further comprising providing the gas detector tube with a dry layer arranged upstream of the absorption layer.

15. A process in accordance with claim 14, wherein the dry layer consists essentially of a carrier material impregnated with sulfuric acid.

16. A process in accordance with claim 12, wherein the display layer has a length between 10 mm and 15 mm and an internal diameter of between 1 mm and 3 mm.

17. A process in accordance with claim 11, wherein a length of the display layer is selected to be such that a change in color takes place in the display layer at a benzene concentration of 0.5 ppm at a sample gas volume of 1.2 L.

18. A process for detecting benzene in a gas sample, the process comprising the steps of:
   providing a gas detector tube with a display layer which consists essentially of a carrier material impregnated with gold(III) oxide;
   passing the gas sample into the gas detector tube such that the gas sample is reacted with the carrier material impregnated with gold(III) oxide; and
   observing a change in color in the display layer to detect benzene in the gas sample.

19. A process in accordance with claim 18, further comprising:
   providing the gas detector tube with an absorption layer for oxidizing toluene and xylene, the absorption layer being arranged upstream of the display layer; and
   providing the gas detector tube with a dry layer arranged upstream of the absorption layer.

20. A process in accordance with claim 19, wherein:
   gold(III) oxide dissolved in sulfuric acid is used as the impregnation of the carrier material of the display layer;
   the absorption layer consists essentially of a carrier material impregnated with sulfuric acid and selenium oxide; and
   the dry layer consists essentially of a carrier material impregnated with sulfuric acid.

* * * * *